US008390533B2

(12) United States Patent
Yamamoto (10) Patent No.: US 8,390,533 B2
(45) Date of Patent: Mar. 5, 2013

(54) BEAM-SCAN DISPLAY APPARATUS, DISPLAY METHOD, AND VEHICLE

(75) Inventor: Kakuya Yamamoto, Hyogo (JP)

(73) Assignee: Panasonic Corporation, Osaka (JP)

( * ) Notice: Subject to any disclaimer, the term of this patent is extended or adjusted under 35 U.S.C. 154(b) by 726 days.

(21) Appl. No.: 12/523,365

(22) PCT Filed: Nov. 19, 2008

(86) PCT No.: PCT/JP2008/003373
§ 371 (c)(1),
(2), (4) Date: Jul. 16, 2009

(87) PCT Pub. No.: WO2009/066446
PCT Pub. Date: May 28, 2009

(65) Prior Publication Data
US 2010/0045571 A1    Feb. 25, 2010

(30) Foreign Application Priority Data

Nov. 20, 2007   (JP) .................. 2007-300127

(51) Int. Cl.
*G09G 5/00* (2006.01)
(52) U.S. Cl. .............. 345/7; 345/8; 345/9; 359/630; 349/11; 349/13; 349/14
(58) Field of Classification Search .......... 345/7–9; 359/630, 13; 349/11, 13, 14
See application file for complete search history.

(56) References Cited

U.S. PATENT DOCUMENTS

| | | | | |
|---|---|---|---|---|
| 4,162,122 A | * | 7/1979 | Cohen .......... | 351/159.41 |
| 4,637,697 A | * | 1/1987 | Freeman ........ | 351/159.44 |
| 5,175,651 A | * | 12/1992 | Marron et al. ..... | 359/721 |
| 5,355,181 A | | 10/1994 | Ashizaki et al. | |
| 5,508,759 A | | 4/1996 | Konishi et al. | |
| 5,997,140 A | * | 12/1999 | Zhang et al. ..... | 351/159.05 |
| 6,087,941 A | * | 7/2000 | Ferraz ......... | 340/575 |
| 6,229,503 B1 | * | 5/2001 | Mays et al. ...... | 345/7 |
| 6,353,422 B1 | * | 3/2002 | Perlman ........ | 345/7 |

(Continued)

FOREIGN PATENT DOCUMENTS

| | | |
|---|---|---|
| JP | 4-100088 | 4/1992 |
| JP | 2932636 | 8/1999 |

(Continued)

OTHER PUBLICATIONS

International Search Report issued Dec. 16, 2008 in the International (PCT) Application of which the present application is the U.S. National Stage.

*Primary Examiner* — Lun-Yi Lao
*Assistant Examiner* — Kelly B Hegarty
(74) *Attorney, Agent, or Firm* — Wenderoth, Lind & Ponack, L.L.P.

(57) ABSTRACT

A beam-scan display apparatus (10) displays an image by scanning a beam on a retina of a user, the beam-scan display apparatus (10) includes a case (11) housing (i) a light source (101) emitting a beam for drawing each of pixels constituting the image, and (ii) a scan unit (103) two-dimensionally scanning the beam emitted from the light source (101). Further, the beam-scan apparatus includes a contact lens (12) having a deflection unit (104) deflecting, toward the retina of an eye of the user wearing the case (11), the beam scanned by the scan unit (103), wherein the contact lens (12) is separate from the case (11).

16 Claims, 8 Drawing Sheets

U.S. PATENT DOCUMENTS

| | | |
|---|---|---|
| 6,600,460 B1 * | 7/2003 | Mays, Jr. ............................ 345/7 |
| 6,614,408 B1 * | 9/2003 | Mann ................................. 345/8 |
| 7,375,701 B2 * | 5/2008 | Covannon et al. ................. 345/8 |
| 2001/0050751 A1 * | 12/2001 | Banyai et al. ................... 351/168 |
| 2002/0093701 A1 * | 7/2002 | Zhang et al. ..................... 359/15 |
| 2002/0163483 A1 * | 11/2002 | Crist .................................. 345/7 |
| 2005/0099594 A1 * | 5/2005 | Blum et al. ................. 351/160 R |
| 2005/0270474 A1 * | 12/2005 | Odhner ............................ 351/41 |
| 2006/0012752 A1 * | 1/2006 | Chen .............................. 351/177 |
| 2006/0227067 A1 * | 10/2006 | Iwasaki ............................. 345/8 |
| 2008/0002262 A1 * | 1/2008 | Chirieleison .................. 359/630 |
| 2010/0079356 A1 * | 4/2010 | Hoellwarth ....................... 345/8 |

FOREIGN PATENT DOCUMENTS

| | | |
|---|---|---|
| JP | 2995876 | 12/1999 |
| JP | 3425818 | 5/2003 |
| JP | 2005-070671 | 3/2005 |
| JP | 2005-311823 | 11/2005 |
| JP | 2006-98820 | 4/2006 |
| JP | 2006-098820 | 4/2006 |

* cited by examiner

BEAM-SCAN DISPLAY APPARATUS, DISPLAY METHOD, AND VEHICLE

TECHNICAL FIELD

The present invention relates to a display apparatus such as a head-mounted display (HMD).

BACKGROUND ART

One of conventional methods used for display apparatuses such as head-mounted displays (HMDs) is a method of directly drawing images on the retinas of the user's eyes by two-dimensionally scanning laser beams (hereinafter, described as a laser scanning method) (for example, see Patent Reference 1). The display apparatus according to the laser scanning method is also known as a retinal scanning display (RSD), retinal irradiation display, retinal direct-drawing display, laser scanning display, direct-view-type display, virtual retinal display (VRD), and so on.

Further, an eyeglass-type HMD according to the laser scanning method has also been proposed (for example, see Patent Reference 2).

Furthermore, although it is different from the HMD and the laser scanning method, a method for wearing a display apparatus on eyes like contact lenses has also been proposed (for example, see Patent Reference 3).

Moreover, to detect the user's line of sight, there is a method of using reflection of infrared light projected onto the user's eyes (for example, see Patent Reference 4), and a method of using reflection of a laser beam scanned on the user's eyes (for example, see Patent Reference 5).

Patent Reference 1: Japanese Patent No. 2932636
Patent Reference 2: Japanese Unexamined Patent Application Publication No. 2005-70671
Patent Reference 3: Japanese Unexamined Patent Application Publication No. 2005-311823
Patent Reference 4: Japanese Patent No. 2995876
Patent Reference 5: Japanese Patent No. 3425818

DISCLOSURE OF INVENTION

Problems that Invention is to Solve

For those users who do not regularly wear eyeglasses, such as those wearing contact lenses because they dislike eyeglasses, eyeglass-type HMDs sometimes create problems with wearing. For example, there is a problem that the user dislikes his or her own appearance when wearing eyeglasses, a problem of eyeglasses leaving a mark on the user's nose and so on, and a problem of makeup coming off from areas such as the user's nose where eyeglasses are in contact. These problems with eyeglasses also apply to eyeglass-type HMDs.

Patent Reference 3 proposes a contact lens-type display apparatus to avoid the problems with wearing eyeglasses. The method of Patent Reference 3, however, is a method in which the contact lens includes a light source, an optical waveguide, and a propagated light emission unit that are arranged two-dimensionally, which still leaves many problems that hinder its implementation, such as problems regarding miniaturization, ensuring of light transmission, and power supply.

The present invention is to solve the above problems, and it is an object of the present invention to implement, with a laser-scan display, a laser-scan display apparatus that solves the problems regarding wearing.

Means to Solve the Problems

In order to solve the conventional problems, the beam-scan display apparatus according to an aspect of the present invention is a beam-scan display apparatus that displays an image by scanning a beam on a retina of a user, the beam-scan display apparatus comprising: a case for housing (i) a light source which emits a beam for drawing each of pixels constituting the image, and (ii) a scan unit configured to two-dimensionally scan the beam emitted from the light source; and a contact lens having a deflection unit configured to deflect, toward the retina of an eye of the user wearing the case, the beam scanned by the scan unit, the contact lens being separate from the case. Having the case and the contact lens separately as in the above structure solves the problems with wearing eyeglass-type HMDs, and produces an advantageous effect of avoiding a change in the user's appearance caused by wearing eyeglasses.

Further, the deflection unit may be a hologram formed on a surface of the contact lens. This structure makes the deflection unit thinner, thereby allowing the contact lens to be worn more comfortably. Further, the diffraction angle selectivity produces an advantageous effect of displaying images on the retina even when a change in the relative positional relationship between the scan unit and the deflection unit causes a change in the incidence angle at which the beam is incident on the deflection unit. In addition, the diffraction frequency selectivity allows light of a laser color and light of other colors to have different diffraction angles, which makes it possible to provide a see-through display apparatus which enables the user to view the display while seeing external views.

Furthermore, the hologram may have: a first interference pattern for deflecting, toward the user's retina, a beam incident from a first direction; and a second interference pattern for deflecting, toward the user's retina, a beam incident from a second direction different from the first direction.

As an embodiment, the first and second directions are directions from the scan unit toward the hologram before and after the contact lens rotates along a surface of an eyeball of the user by a predetermined angle. This structure allows deflection, toward the user's retina, of the beam scanned by the scan unit even when the contact lens rotates while worn, thereby producing an advantageous effect of reducing the occurrence of a situation where the user cannot see images.

As another embodiment, the first and second directions are directions from the scan unit toward the hologram before and after the contact lens revolves around a center of an eyeball of the user by a predetermined angle. This structure allows deflection, toward the retina, of the beam scanned by the scan unit even when the contact lens moves with turning of the user's eyeball, thereby producing an advantageous effect of enabling the user to see images.

Further, the contact lens may include a rotation suppressing part which suppresses rotation of the contact lens along a surface of an eyeball of the user. With this structure, the contact lens is less likely to rotate while worn, thereby producing an advantageous effect of reducing the occurrence of a situation where the user cannot see images due to the rotation of the contact lens.

Furthermore, the rotation suppressing part may be a part of the contact lens, and may have a density different from a density of an other part of the contact lens. This structure easily allows the contact lens to have a characteristic of suppressing its rotation, thereby producing an advantageous effect of inexpensively and promptly reducing the occurrence of a situation where the user cannot see images due to the rotation of the contact lens.

Moreover, the beam-scan display apparatus according to an aspect of the present invention further comprises: a light detection unit configured to detect reflection, from the contact lens, of the beam emitted from the light source; a relative position detection unit configured to detect a change in relative positions of the scan unit and the deflection unit with respect to each other, based on the detection by the light detection unit; and a scan angle control unit configured to control a scan angle of the scan unit based on the detection by the relative position detection unit such that the beam incident on the deflection unit travels toward the user's retina. This structure makes it easier to detect the position of the contact lens using the light reflected from the contact lens, thereby producing an advantageous effect of reducing deterioration of displayed images caused by a change in the position, such as deterioration in image quality and image displacement.

Further, the contact lens includes a characteristic point having a reflection property different from a reflection property of an other part of the contact lens. The light detection unit is configured to detect light reflected from the characteristic point. Further, the relative position detection unit may be configured to detect a change in the relative positions of the scan unit and the deflection unit based on a difference between a predetermined reference position of the characteristic point and a position of the characteristic point detected by the light detection unit. This structure makes it easier to detect the positional relationship between the scan unit and the contact lens, thereby producing an advantageous effect of reducing deterioration of displayed images caused by a change in the positions, such as deterioration in image quality and image displacement.

Further, the characteristic point may be provided closer to the scan unit than a vertex of the contact lens. This enables the light detection unit to reliably detect the position of the characteristic point.

Furthermore, the scan unit may be provided more forward than the deflection unit with respect to the user. This structure makes it possible to decrease the incidence angle at which the beam is incident on the deflection unit, thereby producing an advantageous effect of enhancing the diffraction efficiency of the hologram, and thus increasing the image quality and making the display screen larger. In addition, since it is possible to reduce the occurrence of a situation where the beam is shielded by the skin and so on, there is an advantageous effect that a situation where the user cannot see images is less likely to occur.

Furthermore, the scan unit may be provided more downward than the deflection unit with respect to the user. This structure makes it possible to reduce the occurrence of a situation where the beam is shielded by the user's upper eyelid, thereby producing an advantageous effect that a situation where the user cannot see images is less likely to occur. In addition, it is possible to reduce the occurrence of a situation where the scan unit shields the user's line of sight when the user sees an object at a position equivalent to that of his or her eye. Therefore, there is an advantageous effect of preventing the display apparatus from shielding the user's line of sight when he or she sees another person's face or eyes. Likewise, when the user shows his or her face to another person, the user's eyes can be seen by the person without being shielded by the display apparatus.

Moreover, the scan unit may be provided between an ear of the user and the deflection unit in a horizontal direction of a head of the user. With this structure, providing the left-eye scan unit to the left of the user's left eye produces an advantageous effect that the scan unit is less likely to shield the user's central visual field when the user faces the front. The same advantageous effect can be produced also when the right-eye scan unit is provided to the right of the user's right eye. Furthermore, providing the left-eye scan unit to the right of the user's left ear makes it possible to shorten the distance between the scan unit and the deflection unit, thereby producing an advantageous effect of miniaturizing the scan mirror of the scan unit because the beam diameter necessary for the scan unit can be reduced in some cases. When the size of the scan mirror is maintained the same, the shortened distance allows scanning a beam having a larger diameter. As a result, the size of the beam focused on the retina can be made smaller, which produces an advantageous effect that images can be displayed with higher resolution. The same advantageous effect can be produced also when the right-eye scan unit is provided to the left of the user's right ear.

Further, the case may be supported only by a temporal region of the user. This structure makes the display apparatus non-eyeglass-type, thereby solving the problems with wearing eyeglasses. As a result, an advantageous effect is produced that wearing the apparatus does not leave a mark on the user's nose and so on, nor does it cause makeup to come off from contact areas such as the user's nose.

Furthermore, the case may include: a first part located in front of a contact position, the contact position being in contact with the user's temporal region; and a second part located behind the contact position such that about the contact position, a moment of the first part and a moment of the second part are substantially in equilibrium. With this structure, the center of gravity of the case is around a temporal-region contact position, that is, a position in contact with the temporal region near the user's ear, thereby producing an advantageous effect of reducing the occurrence of the apparatus displacement and thus reducing deterioration in the image quality caused by the apparatus displacement. In addition, having the center of gravity near the contact position lightens the weight that the user feels.

Further, the contact position is at a base of an ear of the user. The second part may be provided with a battery for driving the beam-scan display apparatus. With this structure, the center of gravity of the case including the battery is around the temporal-region contact position near the user's ear, thereby producing an advantageous effect of reducing the occurrence of the apparatus displacement and thus reducing deterioration in the image quality caused by the apparatus displacement. In addition, having the center of gravity near the contact position lightens the weight that the user feels.

The display method according to an aspect of the present invention is a method for displaying an image using a beam-scan display apparatus, wherein the beam-scan display apparatus includes: a case for housing a light source and a scan unit; and a contact lens which includes a deflection unit and is separate from the case, and the method comprises: emitting, from the light source, a beam for drawing each of pixels constituting the image; two-dimensionally scanning the beam emitted in the emitting; deflecting, toward a retina of an eye of a user, the beam scanned in the scanning, the deflecting being performed by the deflection unit; detecting reflection, from the contact lens, of the beam emitted in the emitting; detecting a change in relative positions of the scan unit and the deflection unit with respect to each other, based on the detection in the detecting of reflection; and controlling a scan angle of the scan unit based on the detection in the detecting of a change in relative positions such that the beam incident on the deflection unit travels toward the user's retina.

It is to be noted that the present invention can be implemented not only as a beam-scan display apparatus as described above, but also as an integrated circuit which implements the functions of the beam-scan display apparatus, and as a program causing a computer to execute such functions. Furthermore, it is apparent that such a program can be distributed through a recoding medium such as a CD-ROM and a transmission medium such as the Internet. In addition, the present invention can also be implemented as an integrated circuit which implements the functions of the display apparatus as above.

The vehicle according to an aspect of the present invention is a vehicle mounted with the beam-scan display apparatus described above, the vehicle comprising: a driver seat on which a driver wearing the contact lens is seated; and a case holding unit configured to hold the case at a position where a beam can be scanned on the contact lens worn by the driver.

Effects of the Invention

According to the present invention, a case for housing a light source and others is provided separately from a contact lens having a deflection unit, thereby achieving a laser-scan display apparatus which can be worn more usefully and comfortably.

NUMERICAL REFERENCES

10 Beam-scan display apparatus
11 Case
12 Contact lens
101 Light source
102 Wavefront shape change unit
103, 103A, 103B, 103C Scan unit
104 Deflection unit
105 Control unit
106 Headphone unit
106A Speaker
106B Battery
201 Focal length horizontal component change unit
202 Focal length vertical component change unit
211 Red laser light source
212 Blue laser light source
213 Green laser light source
214 Light detection unit
401 Rotation suppressing part
501 Central processing unit
501a Relative position detection unit
501b Scan angle control unit
502 Memory unit
503 Input/output control unit
510 Light source input/output control unit
511 Wavefront-shape-change input/output control unit
512 Scan input/output control unit
513 Deflection input/output control unit
514 Headphone input/output control unit
515 Power source input/output control unit
516 Communication input/output control unit
520 Communication unit
601A, 601B Characteristic point
1000 Vehicle
1001 Driver seat
1002 Case holding unit

BEST MODE FOR CARRYING OUT THE INVENTION

Hereinafter, embodiments of the present invention shall be described with reference to the drawings.

Embodiment 1

Figure 1:
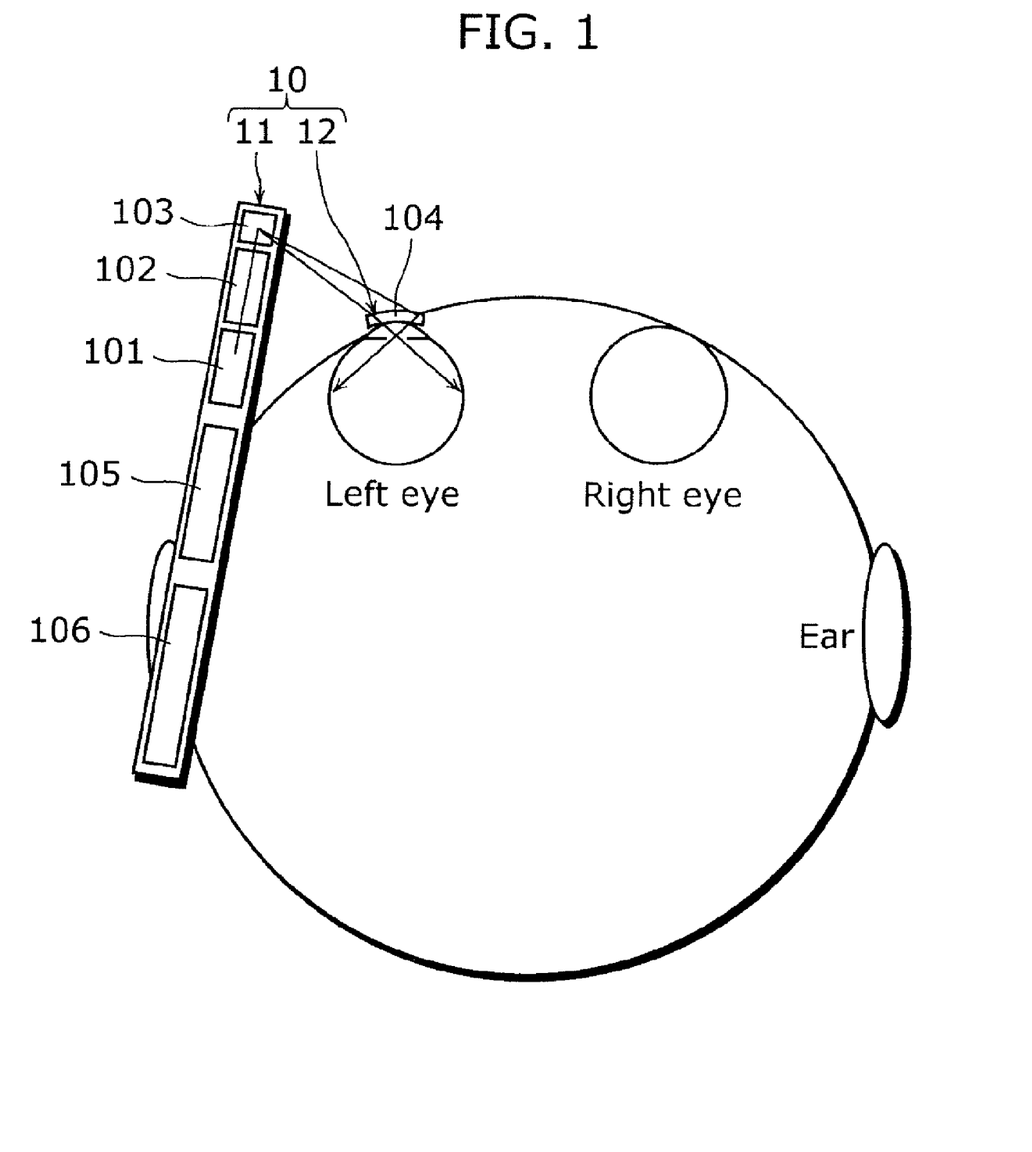
FIG. 1 is a plan view of a beam-scan display apparatus according to Embodiment 1 of the present invention.
Figure 2:
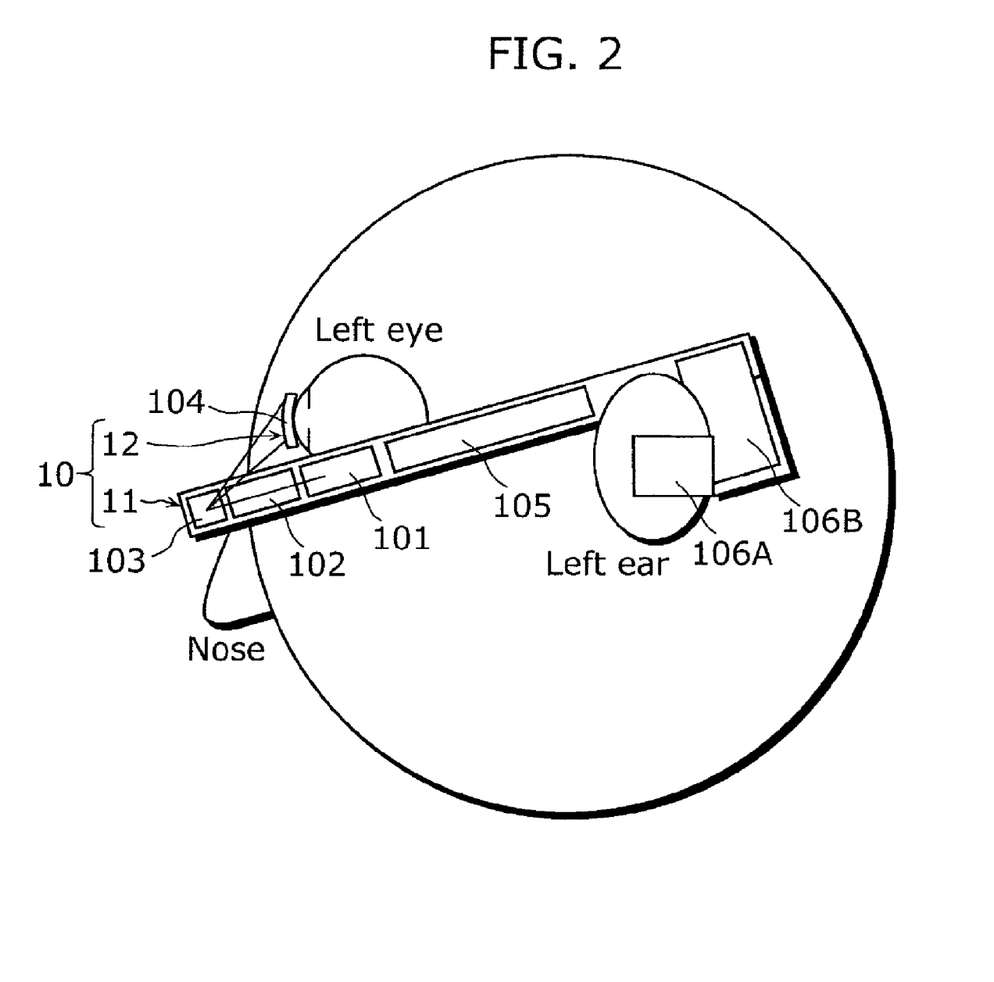
FIG. 2 is a side view of a beam-scan display apparatus according to Embodiment 1 of the present invention.
Figure 3:
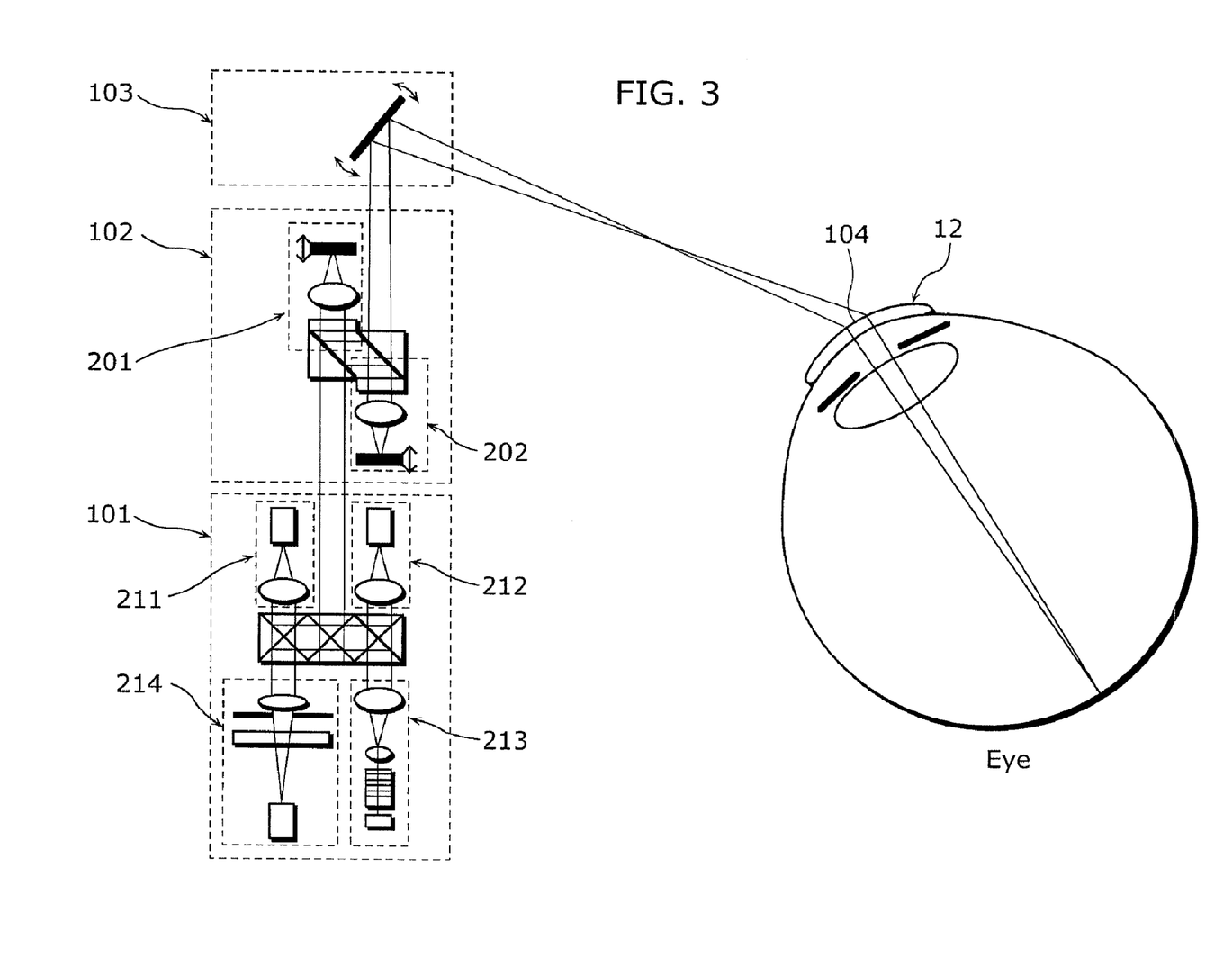
FIG. 3 is a detail structural diagram of a beam-scan display apparatus according to Embodiment 1 of the present invention.
Figure 4:
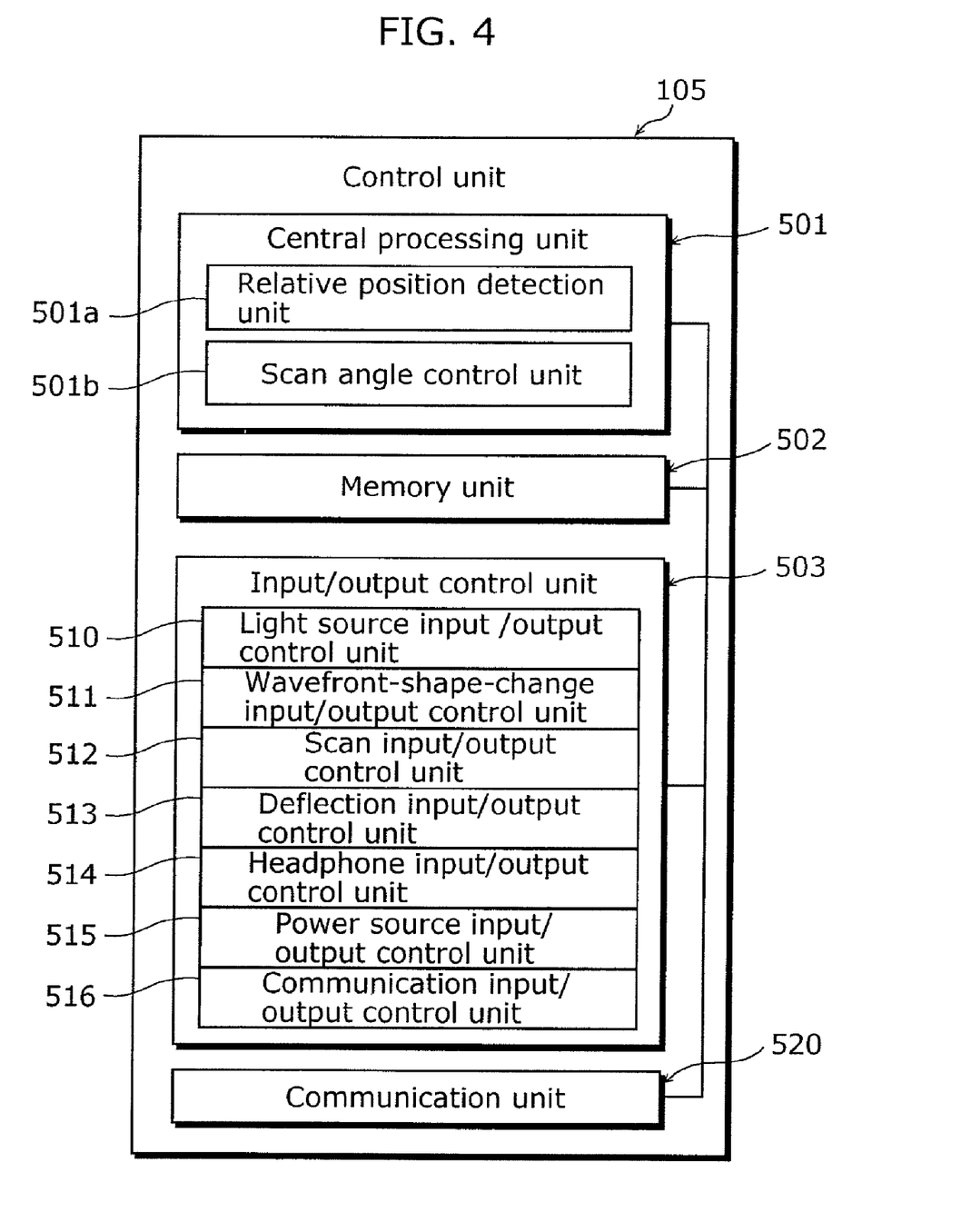
FIG. 4 is a structural diagram of a control unit of a beam-scan display apparatus according to Embodiment 1 of the present invention.

With reference to FIGS. 1 to 4, a beam-scan display apparatus 10 according to Embodiment 1 of the present invention shall be described. It is to be noted that FIG. 1 is a plan view of the beam-scan display apparatus 10, FIG. 2 is a side view of the beam-scan display apparatus 10, FIG. 3 is a detail structural diagram of a portion of FIG. 1, and FIG. 4 is a functional block diagram of the beam-scan display apparatus 10.

First, as shown in FIGS. 1 and 2, the beam-scan display apparatus 10 includes a case 11 fixed to a user's temporal region and a contact lens 12 worn on the user's eye, and displays images by scanning the beam on the user's retina. As apparent from FIGS. 1 and 2, the case 11 and the contact lens 12 are components independent (separate) from each other.

The case 11 includes a light source 101, a wavefront shape change unit 102, a scan unit 103, a control unit 105, and a headphone unit 106. It is to be noted that the headphone unit 106 in the present embodiment includes, as shown in FIG. 2, a speaker 106A which outputs audio and a battery 106B which drives the beam-scan display apparatus 10. Meanwhile, the contact lens 12 is provided with a deflection unit 104 on its surface.

The light source 101 emits a beam for drawing each of pixels constituting an image. As shown in FIG. 3, the beam emitted is a laser beam obtained by synthesizing laser beams emitted from a red laser light source 211, a blue laser light source 212, and a green laser light source 213. A laser beam of an arbitrary color can be emitted through appropriate modulation of the output from the laser light sources 211, 212, and 213. Furthermore, through modulation in coordination with the wavefront shape change unit 102, scan unit 103, and so on, it is possible to display an image on the retina of the user's eye.

In FIG. 3, the red laser light source 211 is a semiconductor laser light source which emits a red laser beam, and the blue laser light source 212 is a semiconductor laser light source which emits a blue laser beam. In contrast, the green laser light source 213 is structured by combining a semiconductor laser light source that emits an infrared ray and a second-harmonic generation (SHG) device that converts the infrared ray into a green laser beam. The green laser light source 213, however, is not limited to the above, and it may be a semiconductor laser light source that emits a green laser beam. In addition, each laser light source may also be a solid-state laser, a liquid laser, a gas laser, or a light-emitting diode.

It should be noted that in FIG. 3, laser beams are modulated by each of the laser light sources 211, 212, and 213; however, for modulating the laser beams, an intensity modulation unit which modulates the laser beams emitted from each of the laser light sources 211, 212, and 213 may also be used in combination with the laser light sources 211, 212, and 213. With this, even the laser light sources 211, 212, and 213 which emit a laser beam at a constant intensity can be applied to the present invention by being combined with the intensity modulation unit.

The light source 101 may further include a light detection unit 214. The light detection unit 214 detects the position of the contact lens 12 and the user's line-of-sight direction by detecting the intensity of light reflected from the contact lens 12 and light reflected from the cornea of the user's eye. Most of the beams deflected by the deflection unit 104 toward the user's eye obliquely enter the surface of the cornea, whereas a beam from the front of the user's eyeball perpendicularly enters the surface of the cornea. Thus, the reflectance of the beam from the front of the user's eyeball is relatively higher. In view of the above, the detection of the intensity of the reflected light allows the detection of the line-of-sight direction. The operations in the detections of the contact lens 12 and the line-of-sight direction shall be described in the descriptions of operations provided later.

The wavefront shape change unit 102 changes the wavefront shape of the beam emitted from the light source 101 such that the spot size of the beam deflected by the deflecting unit 104 falls within a predetermined range. It is to be noted that the "spot size" of a beam, which is hereinafter described as the spot size on the retina of the user's eye, may be the spot size on the pupil or cornea, or the spot size on the deflection unit. The spot size on the retina is the same as the size of a pixel to be displayed. Further, the "wavefront shape" is a three-dimensional shape of a beam wavefront, and includes planar, spherical, and aspherical shapes.

As shown in FIG. 3, the wavefront shape change unit 102 has a focal length horizontal component change unit 201 and a focal length vertical component change unit 202 arranged in series on an optical path. This makes it possible to separately change the horizontal and vertical curvatures of the beam. The focal length horizontal component change unit 201 changes the horizontal curvature by changing the distance between a cylindrical lens and a mirror. The focal length vertical component change unit 202 changes the vertical curvature by using a cylindrical lens provided perpendicular to the cylindrical lens of the focal length horizontal component change unit 201. In addition, both the focal length horizontal component change unit 201 and focal length vertical component change unit 202 change the beam diameter along with the change of the curvature.

Note that it is possible to adapt to the horizontal change more largely by changing the horizontal curvature more largely than the vertical curvature. This is particularly effective in the case where the horizontal view angle of the screen is intended to be made larger than the vertical view angle, or where the horizontal incidence angle at which the beam is incident on the deflection unit 104 from the scan unit 103 is larger than the vertical incidence angle, as in the case of having the scan unit 103 on the temporal region.

In FIG. 3, of the items representing wavefront shapes, only the horizontal curvature, vertical curvature, and the respective diameters thereof are changed. However, a unit may be provided which changes other items such as the distribution of curvatures within the wavefront, or the shape or size of the wavefront edge. This produces advantageous effects of correcting aberration of the beams reaching the retina and of changing the beam shape.

The wavefront shape change unit 102 in FIG. 3 changes the wavefront shape by using a cylindrical lens and a mirror; however, a variable shape lens such as a liquid-crystal lens and a liquid lens, a diffractive device, or an electro-optic (EO) conversion device may also be used as other means.

The scan unit 103 two-dimensionally scans the beam processed by the wavefront shape change unit 102. The scan unit 103 is a single-plate small mirror which can change angles two-dimensionally. More specifically, the scan unit 103 is a micro-electro-mechanical-system (MEMS) mirror.

It is to be noted that the scan unit 103 may be implemented as a combination of two or more types of scan units, such as a horizontal scan unit and a vertical scan unit. Separately having the horizontal scan unit and the vertical scan unit produces advantageous effects that the oscillation of one of the scan units does not easily influence the other scan unit, and the mechanisms of the scan units can be simplified.

The use of the scan unit 103 is not limited to a method in which the mirror is physically tilted. The scan unit 103 may also be applied to a method in which lenses are moved or diffractive devices are rotated, and a method in which variable shape lenses such as liquid-crystal lenses, or diffractive devices such as acousto-optic (AO) devices and electro-optic (EO) conversion devices are used.

The deflection unit 104 deflects, toward the user's eye, the beam scanned by the scan unit 103. The deflection unit 104 is designed so as to diffract, toward the retina of the user's eye, the beam scanned by the scan unit 103, by forming, for example, a photopolymer layer on the surface of the contact lens 12 and then forming a Lippmann volumetric hologram on the photopolymer layer.

In the photopolymer layer, three holograms may be multiply-formed to reflect red, green and blue beams emitted from the respective laser light sources, or a trilayer hologram which corresponds to the beams of the respective colors may be laminated. Further, it is possible to provide a see-through display by designing it using wavelength selectivity of a hologram such that it diffracts only the light having the wavelength of the light source and does not diffract the light accounting for the major part of the light from the external world and having wavelengths other than the wavelength of the light source. Deflecting the beam through the diffraction by the hologram allows the deflection unit 104 to be thinner, and thus the discomfort of wearing the contact lens 12 can be solved.

The contact lens 12 may have no corrective power. Further, the deflection unit 104 is not limited to a diffractive device such as a hologram, but may also be a mirror such as a concave mirror, or a lens such as a convex lens.

The control unit 105 includes an integrated circuit that controls each unit of the HMD. As shown in FIG. 4, the control unit 105 may include a central processing unit 501, a memory unit 502, an input/output control unit 503, and a communication unit 520.

The central processing unit 501 includes: a relative position detection unit 501a which detects, based on the reflected light detected by the light detection unit 214, a change in relative positions of the scan unit 103 and the deflection unit 104 with respect to each other; and a scan angle control unit 501b which controls, based on the detection by the relative position detection unit 501a, the scan angle of the scan unit 103 such that the beam incident on the deflection unit 104 travels toward the retina.

The memory unit 502 stores data used by the control unit 105.

The input/output control unit 503 controls input and output of control signals to and from the light source 101, wavefront shape change unit 102, scan unit 103, deflection unit 104, headphone unit 106, battery 106B, communication unit 520, and so on which are the targets of the control by the control unit 105. The input/output control unit 503 includes a control unit for each of the control targets, namely, a light source input/output control unit 510, a wavefront-shape-change input/output control unit 511, a scan input/output control unit 512, a deflection input/output control unit 513, a headphone input/output control unit 514, a power source input/output control unit 515, and a communication input/output control unit 516. Execution of the input and output processing by the input/output control unit 503 allows reduction in the processing load on the central processing unit 501. The central processing unit 501 performs information processing by exchanging signals with the memory unit 502 and the input/output control unit 503. The specific method of the control shall be described in the descriptions of operations provided later.

The communication unit 520 is wirelessly connected with a peripheral appliance, such as a mobile phone, to receive video and audio signals. This makes the connection between the HMD and the peripheral appliance a wireless connection, thereby allowing the HMD to be worn more usefully and comfortably.

As shown in FIG. 1, the scan unit 103 may be provided more forward than the deflection unit 104 with respect to the user. This makes it possible to decrease the incidence angle at which the beam is incident on the deflection unit 104, which leads to an advantageous effect of enhanced diffraction efficiency of the hologram, thereby increasing the image quality and making the display screen larger. In addition, since it is possible to reduce the occurrence of the situation where the beam is shielded by the skin and so on, the situation where the user cannot see images is less likely to occur.

As shown in FIG. 2, the scan unit 103 may be provided more downward than the deflection unit 104 with respect to the user. With this, it is possible to reduce the occurrence of the situation where the beam is shielded by the user's upper eyelid, and thus the situation where the user cannot see images is less likely to occur. In addition, the scan unit 103 is less likely to shield the user's line of sight when he or she sees an object at a position equivalent to that of his or her eye. Therefore, there is an advantageous effect of preventing the beam-scan display apparatus 10 from shielding the user's line of sight when he or she sees another person's face or eyes. Likewise, when the user shows his or her face to another person, the user's eyes can be seen by the person without being shielded by the beam-scan display apparatus 10.

As shown in FIG. 1, the scan unit 103 may be provided between the user's ear and the deflection unit 104 in the horizontal direction of the user's head. Providing a left-eye scan unit 103 to the left of the user's left eye produces an advantageous effect that the scan unit 103 is less likely to shield the user's central visual field when the user faces the front. The same advantageous effect can be produced also when a right-eye scan unit is provided to the right of the user's right eye. Furthermore, providing the left-eye scan unit 103 to the right of the user's left ear makes it possible to shorten the distance between the scan unit 103 and the deflection unit 104. As a result, there is an advantageous effect of miniaturizing the scan mirror of the scan unit 103 because the beam diameter necessary for the scan unit 103 can be reduced in some cases. When the size of the scan mirror is maintained the same, the shorter distance allows scanning with a beam having a larger diameter. As a result, the size of the beam focused on the retina can be made smaller, which produces an advantageous effect that images can be displayed with higher resolution. The same advantageous effect can be produced also when the right-eye scan unit is provided to the left of the right ear.

As shown in FIG. 1, the case 11 may be fixed only by the user's temporal region. More specifically, the case 11 may be supported by the base of the ear so that the case 11 is not in contact with the user's nose or forehead. This structure makes the beam-scan display apparatus 10 the non-eyeglass-type, thereby solving the problems with wearing eyeglasses. As a result, there is an advantageous effect that wearing the apparatus does not leave a mark on the user's nose and so on, nor does it cause makeup to come off from contact areas such as the user's nose.

As shown in FIG. 2, the case 11 is structured such that about a temporal-region contact position, that is, a position in contact with the temporal region, the moment of a case front part (a first part) and the moment of a case rear part (a second part) are substantially in equilibrium. Here, the case front part is the part located in front of the temporal-region contact position, and the case rear part is the part located behind the temporal-region contact position. In FIG. 2, the temporal region above the ear is the contact position in contact with the case 11. As a result, the center of gravity of the case 11 is around the temporal-region contact position near the ear. This produces an advantageous effect of reducing the occurrence of the apparatus displacement and thus reducing deterioration in the image quality caused by the apparatus displacement. In addition, having the center of gravity near the contact position lightens the weight that the user feels.

Here, as apparent from FIG. 2, the distance between the temporal-region contact position and the front end of the case front part is longer than the distance between the temporal-region contact position and the rear end of the case rear part. Thus, to achieve an equilibrium of moments between the front and rear parts, the case rear part needs to be heavier than the case front part. In view of the above, the battery 106B, which is the heaviest of all the constituent elements, can be provided in the case rear part.

It is to be noted that the case 11 including the scan unit 103 may be in contact with the user's head as shown in FIG. 1, fixed to a wall, a pole, a desk, a chair, or a desk lamp near the user, or provided in a portable terminal such as a mobile phone.

Each of the units and parts shown in FIGS. 1, 2 and 3, except for the deflection unit 104, may be included in a single case 11 or in plural cases. For example, the light source 101 and the scan unit 103 may be included in separate cases. Further, the headphone unit 106 does not need to be included. In addition, the units may be dispersedly provided. For example, the control unit 105 may be partially included in the scan unit 103 or the wavefront shape change unit 102. Furthermore, each of the units may be plural. For example, there may be two scan units 103 for the left and right eyes. Moreover, the scan unit 103 of the case 11 mounted on the user and another scan unit 103 provided in the public space may scan beams onto the same deflection unit 104. Further, a single scan unit 103 may scan a beam on both the deflection unit 104 for the left eye and the deflection unit 104 for the right eye. Each unit may be shared by plural apparatuses. For example, the light source 101 may be shared by two display apparatuses.

Here, the beam-scan display apparatus 10 of the above structure separately includes the case 11 containing the scan unit 103 and the contact lens 12 containing the deflection unit 104. As a result, movement of the contact lens 12 causes a change in the relative positions of the scan unit 103 and the deflection unit 104 with respect to each other.

Thus, by utilizing the diffraction angle selectivity of the hologram, it is possible to display images on the retina even when a change in the relative positional relationship between the scan unit 103 and the deflection unit 104 causes a change in the incidence angle at which the beam is incident on the deflection unit 104.

The hologram can be generated by forming a photopolymer layer on the surface of the contact lens 12 and then exposing the photopolymer layer to an object beam and a reference beam. At this time, the angle selectivity can be obtained through multiple exposure of the photopolymer layer to plural combinations of an object beam and a reference beam. That is to say, it is possible to provide the angle selectivity to the hologram by forming, through the multiple exposure, a first interference pattern for deflecting, toward the retina, a beam incident from a first direction, and a second interference pattern for deflecting, toward the retina, a beam incident from a second direction different from the first direction.

Figure 5:
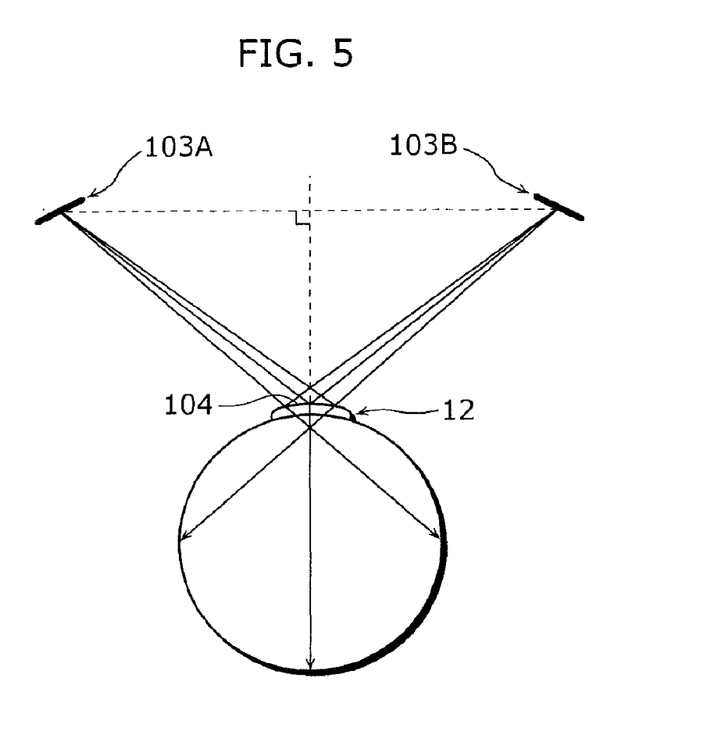
FIG. 5 illustrates an example of a positional relationship between a scan unit and a deflection unit according to Embodiment 1 of the present invention.

FIG. 5 shows relative positions of the scan unit 103 and the deflection unit 104 with respect to each other before and after the contact lens 12 rotates along the surface of the eyeball by a predetermined angle. It is to be noted that although FIG. 5 shows a change in the position of the scan unit 103, the relative positions of the scan unit 103 and the deflection unit 104 are both in fact changed as a result of the rotation of the deflection unit 104.

A scan unit 103A shown in FIG. 5 shows its relative position with respect to the position of the deflection unit 104 when the user wears the beam-scan display apparatus 10. At this time, a first interference pattern allows a beam incident on the deflection unit 104 from the scan unit 103A located diagonally forward left (a first direction), to be deflected toward the user's retina.

On the other hand, a scan unit 103B shows the relative positions of the scan unit 103 and the deflection unit 104 after the contact lens 12 rotates by 180° along the surface of the user's eyeball around, as the rotation axis, the normal line to the vertex of the contact lens 12. At this time, a second interference pattern allows a beam incident on the deflection unit 104 from the scan unit 103B located diagonally forward right (a second direction), to be deflected toward the user's retina.

With such first and second interference patterns, images can be continuously displayed even when the contact lens 12 rotates in the user's eye. It is to be noted that although the above description has illustrated the example of forming just two types of interference patterns for the purpose of simplicity, forming a greater number of interference patterns allows adapting to various rotation angles of the contact lens 12.

Figure 6:
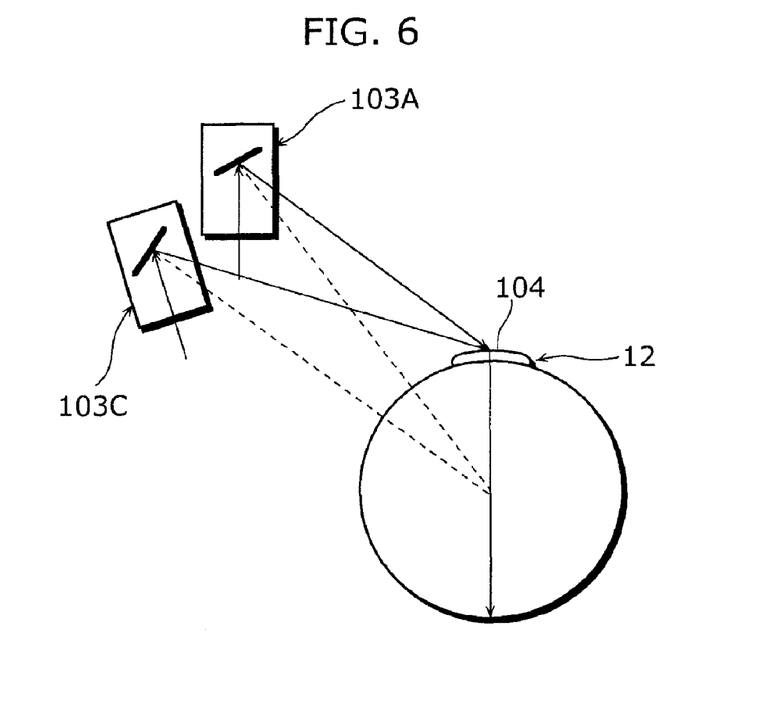
FIG. 6 illustrates another example of a positional relationship between a scan unit and a deflection unit according to Embodiment 1 of the present invention.

Next, FIG. 6 shows relative positions of the scan unit 103 and the deflection unit 104 with respect to each other before and after the contact lens 12 revolves around the center of the eyeball by a predetermined angle. It is to be noted that although FIG. 6 shows a change in the position of the scan unit 103, the relative positions of the scan unit 103 and the deflection unit 104 are both in fact changed as a result of the revolution of the deflection unit 104.

The scan unit 103A shown in FIG. 6 shows its relative position with respect to the position of the deflection unit 104 when the user wears the beam-scan display apparatus 10. Here, a first interference pattern allows a beam incident on the deflection unit 104 from the scan unit 103A located diagonally forward left, that is, from a first direction, to be deflected toward the user's retina.

On the other hand, the scan unit 103C shows the relative positions of the scan unit 103 and the deflection unit 104 after the contact lens 12 revolves around the center of the user's eyeball by a predetermined angle as the user's eyeball rotates. Here, a second interference pattern allows a beam incident on the deflection unit 104 from the scan unit 103C located in a second direction, to be deflected toward the user's retina. The second direction is a direction which makes the incidence angle larger than that made by the first direction.

With such first and second interference patterns, images can be continuously displayed even when the contact lens 12 revolves with the rotation of the user's eyeball. It is to be noted that although the above description has illustrated the example of forming just two types of interference patterns for the purpose of simplicity, forming a greater number of interference patterns allows adapting to various rotation angles of the contact lens 12. In addition, a combination of the interference patterns illustrated with reference to FIGS. 5 and 6 allows adapting to various movements of the contact lens 12.

Figure 7:
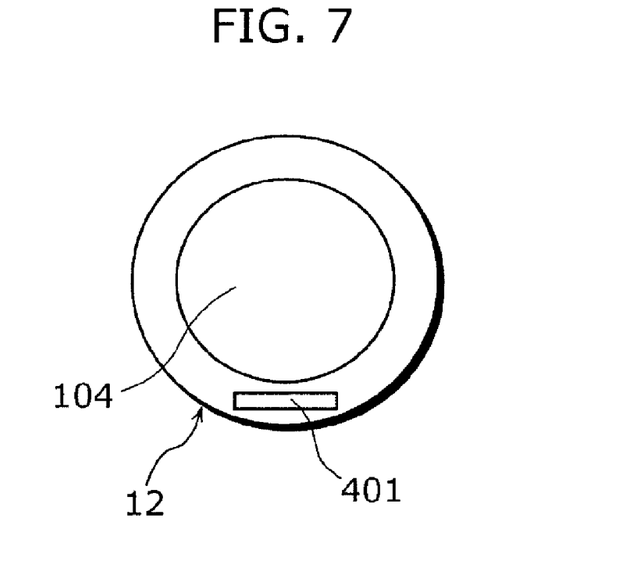
FIG. 7 illustrates an example of a deflection unit according to Embodiment 1 of the present invention.

Next, FIG. 7 illustrates an example of the contact lens 12 according to Embodiment 1.

The contact lens 12 shown in FIG. 7 can be segmented into a central area on which the deflection unit 104 is formed, and an outer edge area which is outside the central area. The outer edge area of the contact lens 12 is provided with a rotation suppressing part 401 which suppresses the rotation of the contact lens 12 along the surface of the user's eyeball.

The rotation suppressing part 401 has a density greater than the average density of the contact lens 12. Thus, when the user wears the contact lens 12, the contact lens 12 rotates in the user's eye such that the rotation suppressing part 401 is positioned downward of the contact lens 12.

With this, the rotation of the contact lens 12 is restricted within a narrow range (angle). It is to be noted that although the rotation suppressing part 401 can be applied alone, a more advantageous effect can be expected by applying the rotation suppressing part 401 in combination with the plural interference patterns illustrated with reference to FIG. 5.

It is to be noted that although Embodiment 1 has illustrated the example of making the density of the rotation suppressing part 401 greater than the average density of the contact lens 12, the present invention is not limited to this. Any form of the rotation suppressing part 401 can be adopted, such as one having a smaller density, as long as the center of the gravity of the contact lens 12 does not come upon the vertex of the contact lens 12.

Furthermore, the method for creating the rotation suppressing part 401 is not specifically limited; a component having a different density may be applied, or a filler such as a resin may be injected into the contact lens 12.

The deflection unit 104 may be formed on a part of the contact lens 12, or on the entire contact lens 12. In the case of forming the deflection unit 104 on a part of the contact lens 12, the manufacturing cost can be reduced since the area for the deflection unit 104 is relatively small. In the case of forming the deflection unit 104 on the entire contact lens 12, the beam-scan display apparatus 10 having a larger screen can be obtained. In the case of forming the deflection unit 104 on a part of the contact lens 12, its position may be, for example, the center, outer surface or inner surface of the contact lens 12. Being positioned at the center allows viewing the display in the central visual field; being positioned on the outer surface allows prevention of a contact between the eye and the deflection unit 104; and being positioned on the inner surface allows prevention of a contact between the external air or the user's eyelid and the deflection unit 104.

Figure 8:
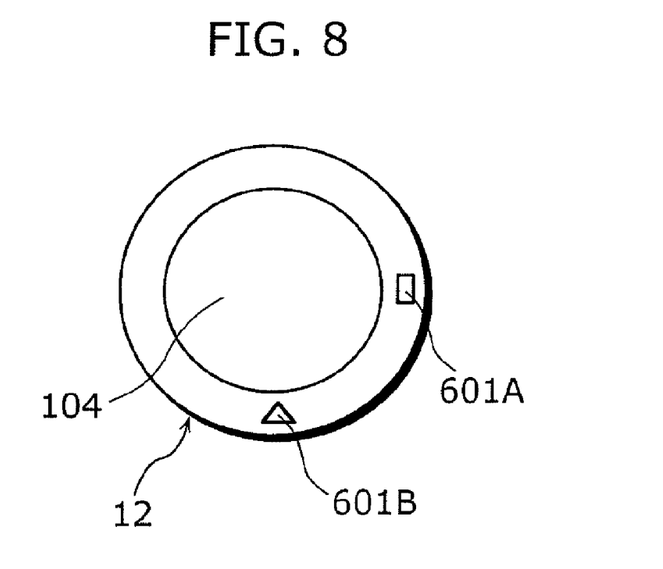
FIG. 8 illustrates another example of a deflection unit according to Embodiment 1 of the present invention.
Figure 9:
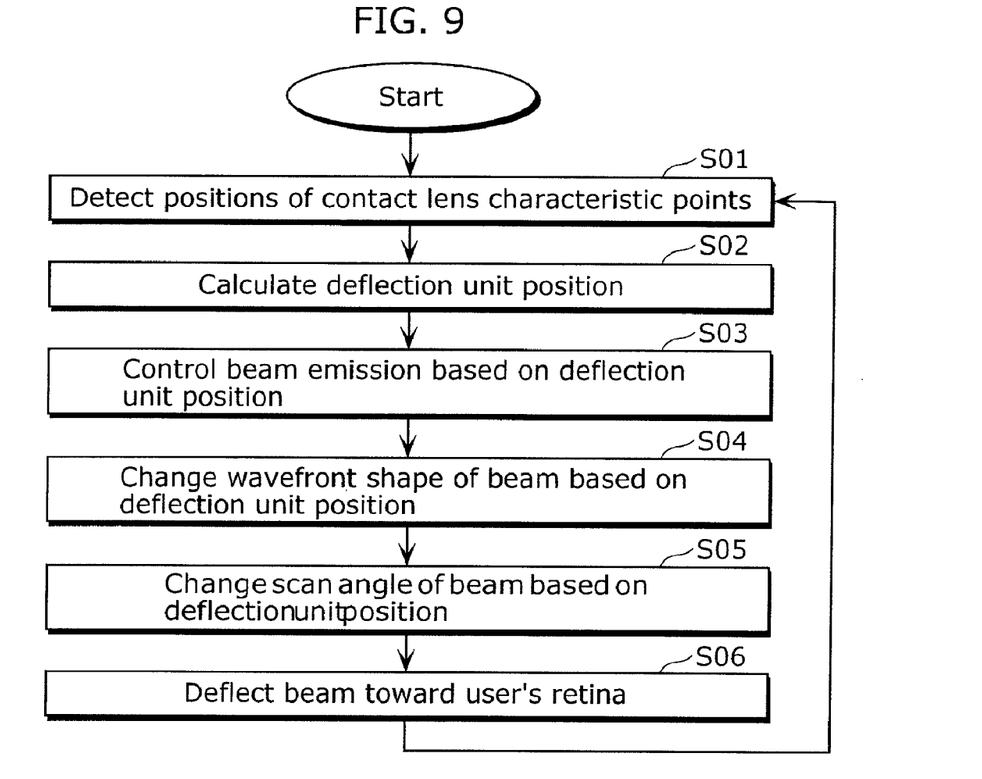
FIG. 9 is a flowchart showing operations of a beam-scan display apparatus according to Embodiment 1 of the present invention.

Next, with reference to FIGS. 8 and 9, another method for solving problems specific to the above beam-scan display apparatus 10 shall be described. FIG. 8 illustrates another example of the contact lens 12 according to Embodiment 1, and FIG. 9 is a flowchart showing operations of the beam-scan display apparatus 10.

The contact lens 12 shown in FIG. 8 can be segmented into a central area on which the deflection unit 104 is formed, and an outer edge area which is outside the central area. The outer edge area of the contact lens 12 is provided with characteristic points 601A and 601B having a reflection property different from that of the rest of the area of the contact lens 12.

It is to be noted that the reflection property of the characteristic points 601A and 601B may be made different from that of the rest of the area of the contact lens 12, using a method of increasing the reflectance by forming a mirror, for example. A higher reflectance allows easier detection. The reflected light may be reflection of a beam used for the display, reflection of infrared light or the like emitted specifically for the detection, or reflection of external light around the user. Further, the reflectance may be decreased by performing processing that causes light scattering. This allows the area having the different reflectance on the contact lens 12 to be inconspicuous. Furthermore, the reflectance with respect to a particular wavelength such as the wavelength of red, black or infrared light, or the reflectance with respect to a combination of such wavelengths may be varied. This allows achieving both the easier detection using laser reflection and the inconspicuousness through low reflection of visible light.

It is to be noted that the characteristic points 601A and 601B may be positioned closer to the scan unit 103 than the center of the contact lens 12. This allows easier detection of the area having a different reflectance, because the optical path of light reflected from the area with the different reflectance to the light detection unit 214 is shortened, and because it is possible to reduce the occurrence of a situation where the area with the different reflectance cannot be detected as the area with the different reflectance moves to a dark part of the other area due to the curvature of the eyeball surface when the user's eyeball rotates.

Next, operations shall be described.

Described with reference to FIG. 9 is a process in which even when the relative positions of the scan unit 103 and the deflection unit 104 change along with the eyeball rotation or the head oscillation, the beam-scan display apparatus 10 shown in FIG. 1 adapts to such a change so as to scan a beam for drawing an image on the user's retina. It is to be noted that the description below is based on the premise that the user is wearing the contact lens 12 shown in FIG. 8.

(S01) The light detection unit 214 detects light reflected from the characteristic points 601A and 601B of the contact lens 12. Then, the process proceeds to the operation in S02. The scan unit 103 scans a beam on the area of the contact lens 12 which includes the deflection unit 104, and a beam reflected from the contact lens 12 reaches the light detection unit 214 via the scan unit 103. Based on a change in the intensity of the reflected light detected and the angle of the scanning by the scan unit 103, the characteristic points 601A and 601B (the relative positions with respect to that of the scan unit 103) are detected. The detection of a change in the reflectance is facilitated by providing an area having a different reflection property, such as the characteristic points 601A and 601B shown in FIG. 8. Furthermore, the distance between the scan unit 103 and the contact lens may be detected by detecting, by the light detection unit 214, the reflected beam diameter, or the curvature radius or the wavefront shape of the beam, in addition to detecting the intensity of the reflected light.

It is to be noted that aside from using the light reflected from the contact lens 12, light reflected from the user's eye, such as from the user's cornea, crystalline lens, or retina, may be used alone or in combination with the light reflected from the contact lens 12. This reduces the impact of a displacement of the contact lens 12 with respect to the user's eyeball. Further, an increased number of types of the reflected light used improves the reliability and precision of the detection.

The position detection in this step may be performed using the reflection of the beam scanned by the scan unit 103 as shown in the present embodiment, or using the reflection of light emitted from a light source different from the light source which emits the beam to be scanned by the scan unit 103. For example, Patent Reference 4 achieves detection of the user's line of sight using an image sensor detecting reflection, from the user's eyes, of infrared light emitted from an infrared-light-emitting diode. Further, Patent Reference 5 achieves detection of the user's line of sight using an image sensor detecting reflection, from the user's eyes, of a beam scanned by a scan unit.

It is to be noted that the intensity of the reflected light may be expressed as a ratio between the intensity of emitted light which has been modulated by the light source 101 and the intensity of the light detected by the light detection unit 214. This reduces the impact of a change in the intensity of the emitted light, caused by a change in the displayed images. Further, while invisible light, such as infrared light, is scanned at a constant intensity, the reflection thereof may be detected. This allows detection of the reflected light independently of changes in the displayed image such as variations in the light/shade or color tone.

(S02) The relative position detection unit 501a of the control unit 105 calculates a deflection unit position, using the positions of the characteristic points 601A and 601B of the contact lens 12 detected in S01. Then, the process proceeds to the operation in S03. The deflection unit position means the relative position of the center of the deflection unit 104 with respect to the center of the scan unit 103. The deflection unit position changes when, for example, the contact lens 12 having the deflection unit 104 moves with an eyeball rotation, or when the case 11 is displaced while worn due to oscillations of the case 11, for instance.

The deflection unit position can be calculated by adding, to a reference position of the deflection unit 104, a difference between the reference position of the deflection unit 104 and the current position of the deflection unit 104. The reference position of the deflection unit 104 is the position of the deflection unit 104 when the line of sight of the user wearing the beam-scan display apparatus 10 is in the front direction. The reference position may be expressed as a value set when the beam-scan display apparatus 10 is designed; a value actually measured when the user purchases the beam-scan display apparatus 10; or a value measured using the light detection unit 214. A value set at the time of designing enables relatively easy implementation; a value measured at the time of purchase enables adapting to differences among individual users; and a value measured by the light detection unit 214 enables adapting to changes that occur during use. In addition, similarly to the reference position of the deflection unit 104, reference positions of the characteristic points 601A and 601B of the contact lens 12 are also calculated based on a positional relationship between the center of the deflection unit 104 and each of the characteristic points 601A and 601B.

The current position of the deflection unit 104 is calculated based on differences between the positions of the characteristic points 601A and 601B of the contact lens 12 detected in S01 and the reference positions of the characteristic points 601A and 601B. In the case of the contact lens 12 having the rotation suppressing part 401 shown in FIG. 7, a change in the positions of the characteristic points 601A and 601B of the contact lens 12 may be considered the same as a change in the position of the deflection unit 104. Further, a change in the position may be calculated with the rotation of the deflection unit 104 taken into account, by detecting the characteristic points 601A and 601B on the respective positions.

In the case of a beam-scan display apparatus 10 which does not include the light detection unit 214, the deflection unit position may be the above mentioned reference position.

(S03) The light source 101 controls the beam emission based on the deflection unit position calculated in S02. Then, the process proceeds to the operation in S04.

Through appropriate modulation of the intensities of the beams emitted from the red laser light source 211, blue laser light source 212, and green laser light source 213, the colors, chrominance, and luminance of pixels to be displayed on the user's retina are represented. In addition, the emission control may be correction control which takes into account the impact of the optical system which includes the components from the light source 101 up to the user's eye, such as the scan unit 103 and the deflecting unit 104. For example, since the beams scanned by the scan unit 103 are obliquely incident on the deflection unit 104, the rectangular shape of the display area is distorted into a non-rectangular shape, such as trapezium. Moreover, a change in the position of the deflection unit 104 influences the degree of the distortion. In view of the above, the light source 101 may control the laser emission in coordination with the scan unit 103 in such a manner that the shape of the display area is inversely corrected in advance to make the display area a rectangle.

It is to be noted that in the case where a movement of the deflection unit 104 causes the deflection unit 104 to be partially hidden and prevents the beam scanned by the scan unit 103 from reaching the deflection unit 104, the beam emission control may be performed such that the beam for the hidden part is not emitted. For example, in the case where the deflection unit 104 is provided in the contact lens 12 of the user's left eye and the scan unit 103 is provided forward left of the left eye, when the user turns his or her left eye to the right to see the right side, a situation could arise where, as an impact of the curvature of the eyeball, the right part of the deflection unit 104 is shielded by the other part, as viewed from the scan unit 103. In such a situation, the output of the light source 101 may be controlled such that the beam is projected only onto the left part of the deflection unit 104.

(S04) Based on the deflection unit position calculated in S02, the wavefront shape change unit 102 changes the wavefront shape of the beam emitted from the light source 101 so that the beam spot size on the user's retina falls within a predetermined range. Then, the process proceeds to the operation in S05. Since the beam spot size on the user's retina varies depending on, for example, the positional relationship between the scan unit 103, the deflection unit 104, and the retina, the wavefront shape of the beam is changed according to a change in the scan angle or deflection unit position. For example, when it is desired to change the horizontal focal length of the wavefront shape, it is changed by altering the distance between the cylindrical lens and the mirror of the focal length horizontal component change unit 201. Likewise, when it is desired to change the vertical focal length of the wavefront shape, it is changed by the focal length vertical component change unit 202.

(S05) The scan angle control unit 501b changes the tilt of the MEMS mirror of the scan unit 103 based on the deflection unit position calculated in S02, so that the scan angle is changed to allow the beam processed by the wavefront shape change unit 102 to travel toward the deflection unit 104. Then, the process proceeds to the operation in Step S06.

Even when there is no change in the deflection unit position, the scan unit 103 changes the scan angle within a predetermined range to scan the beam and display images. When there is a change in the deflection unit position, the range of the scan angle (the upper and lower limits of the scan angle) is additionally changed. When there is also a change in the incident angle at which the beam is incident on the deflection unit 104, the width of the scan angle range (the difference between the upper and lower limits of the scan angle) may also be changed.

(S06) The deflection unit 104 deflects, toward the user's retina, the beam scanned by the scan unit 103. Then, the process proceeds to the operation in S01. The beam deflected due to the diffraction effect of the hologram of the deflecting unit 104 passes through the pupil of the user's eye and reaches the retina to be perceived by the user as an image.

It is to be noted that the series of operations from S03 to S06 may be executed sequentially or concurrently. The execution order of these operations may be rearranged. Easing the restrictions on the execution order increases the possibility of reducing the length of the total process time through multi-thread processing or the like.

It is to be noted that the frequency of executing the operations S01 and S02 may be different from the frequency of executing the operations S03 to S06. The execution of S06 may be followed by the operation in S03. With this, when S01 and S02 consume a long time, it is possible to shorten the total length of time required for repeating the operations S03 to S06 many times.

With the above operations, images can be drawn on the retina of the user's eye while adapting to the changes in the position of the deflection unit 104.

With the beam-scan display apparatus 10 of the present invention with the above structure and operations, the deflection unit 104 is formed on the contact lens 12 worn on the user's eye, thereby solving the problems with wearing the eyeglass-type HMDs. As a result, it is possible to avoid a change in the user's appearance caused by wearing eyeglasses, and wearing the apparatus does not leave a mark on contact areas such as the user's nose nor does it cause makeup to come off from the contact areas such as the user's nose.

It is to be noted that the operations from S01 to S06 may be operations involving probability. For example, the calculation of the deflection unit position may be expressed in probabilities; for instance, the probability that the deflection unit has moved upward by one millimeter is 20%, and the probability that the deflection unit has not moved is 80%. This produces an advantageous effect that even when a calculated value is uncertain, images can be displayed with an image quality higher than that in the case of not performing the calculation.

Embodiment 2

Figure 10:
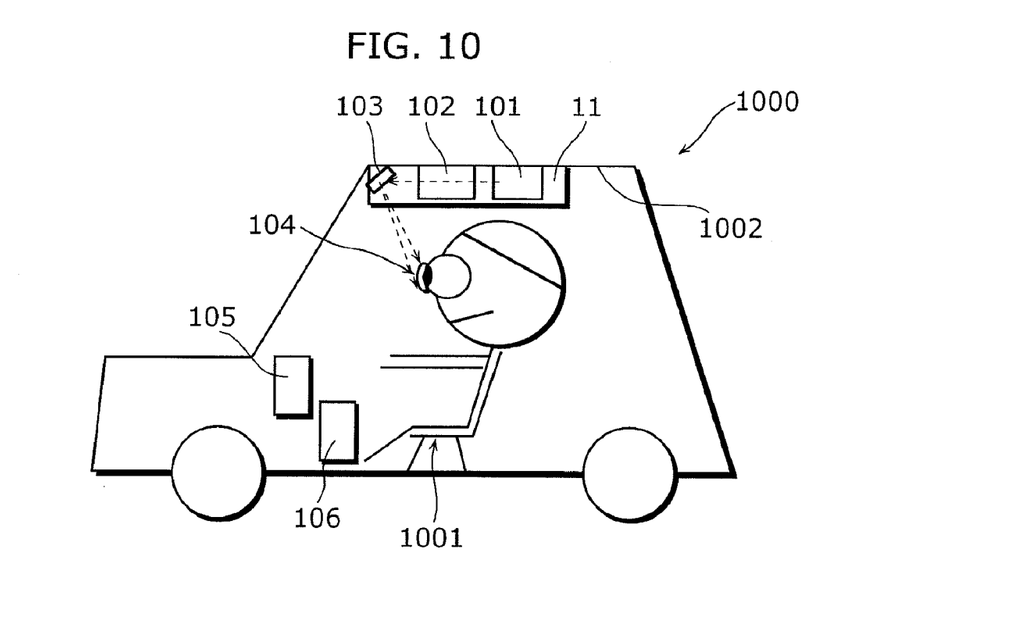
FIG. 10 is a structural diagram of a beam-scan display apparatus according to Embodiment 2 of the present invention.

FIG. 10 is a structural diagram of a Head-Up Display (HUD) for vehicles in Embodiment 2. A vehicle 1000 according to Embodiment 2 includes a driver seat 1001 on which a driver is seated and a case holding unit 1002 which holds the case 11 at a position where a beam can be scanned on the contact lens 12 worn by the driver.

The HUD includes a light source 101, a wavefront shape change unit 102, a scan unit 103, a deflection unit 104, a control unit 105, and a headphone unit 106 which have the same basic structures as those in Embodiment 1, and thus operate in the same manner.

In the present embodiment, images are displayed to a user in a vehicle. As in Embodiment 1, the deflecting unit 104 has a characteristic of deflecting a beam and a characteristic of transmitting visible light from outside the vehicle, which allows the user to view the display according to the present invention while seeing the views outside the vehicle. This allows the user to see information related to, for example, driving actions and a current location, such as a vehicle speed, a caution and alert, and navigation guidance, while seeing the views outside the vehicle.

As shown in FIG. 10, the case 11 holding the light source 101, wavefront shape change unit 102, and scan unit 103 may be provided at a position around the ceiling of the vehicle 1000 (the ceiling corresponds to "the case holding unit 1002"). This prevents shielding the user's visual field seen through the window. Further, since the case 11 is provided at a position close to the user's eyes, the optical path is shortened, thereby enhancing the display precision. In addition, the HUD may be structured such that the light source 101 is provided at a position distant from the wavefront shape change unit 102, such as at the lower part of the vehicle, and beams are transmitted from the light source 101 to the wavefront shape change unit 102 via an optical fiber. This allows reduction in the size of the area on the ceiling, on which the light source 101 is to be provided.

The control unit 105 may be provided inside a dashboard of the vehicle. The control unit 105 may be integrated into a control apparatus other than the beam-scan display apparatus 10 according to the present invention. For example, the control apparatus may be a vehicle speed management apparatus or a guidance control apparatus (car navigation system). This allows a decrease in the total number of control apparatuses.

It is not necessary for the headphone unit 106 to be in contact with the user's ear, and the headphone unit 106 may be a speaker mounted on the interior surface of the vehicle around the user; for example, on a door or the front dashboard of the vehicle.

Embodiment 3

Figure 11:
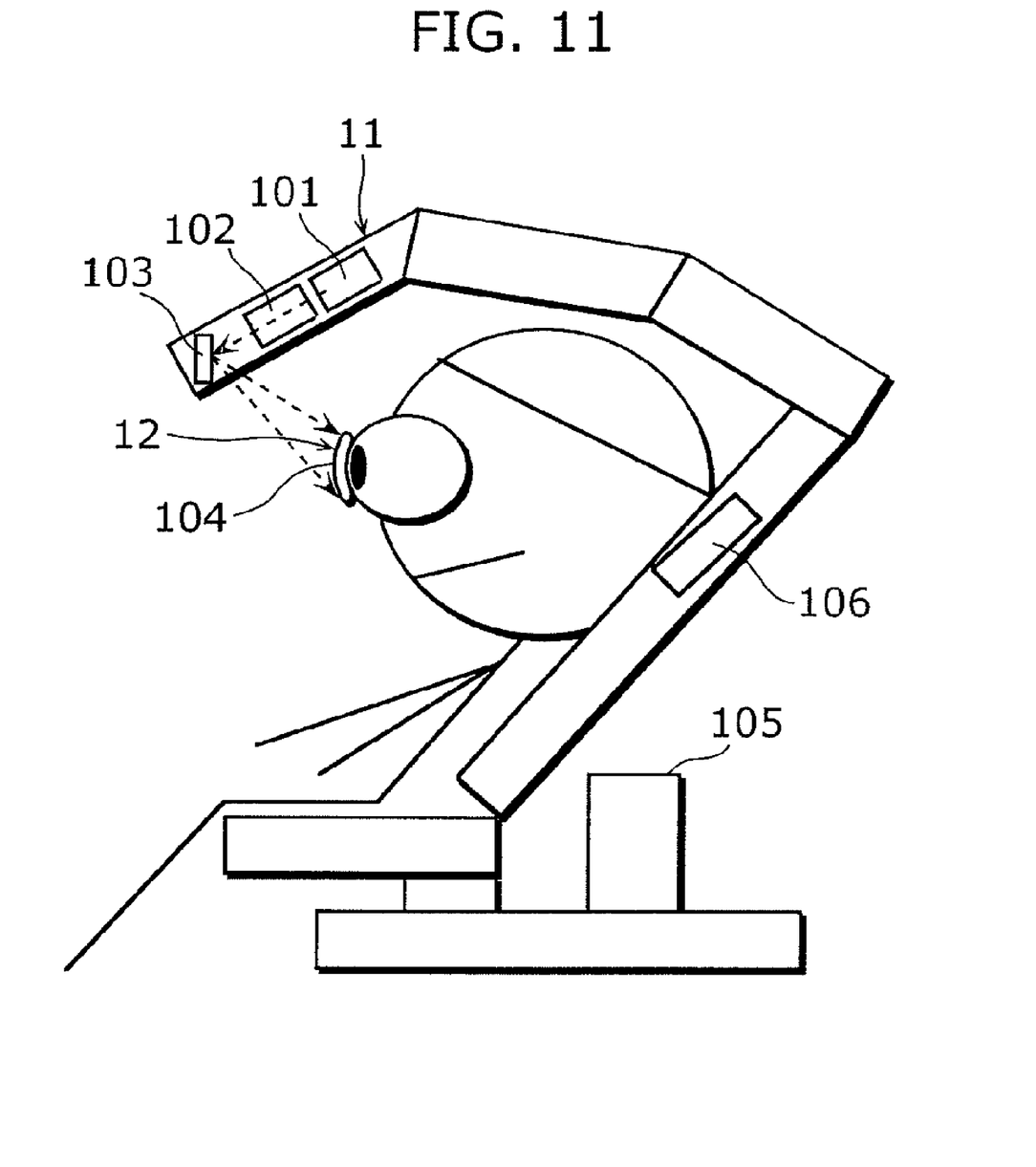
FIG. 11 is a structural diagram of a beam-scan display apparatus according to Embodiment 3 of the present invention.

FIG. 11 is a structural diagram of a chair-type beam-scan display apparatus 10 in Embodiment 3 of the present invention.

The display apparatus includes a light source 101, a wavefront shape change unit 102, a scan unit 103, a deflection unit 104, a control unit 105, and a headphone unit 106 which have the same basic structures as those in Embodiment 1, and thus operate in the same manner.

In the present embodiment, images are displayed to a user seated on a chair.

As shown in FIG. 11, the case 11 including the light source 101, wavefront shape change unit 102, and scan unit 103 may be provided on an area (corresponding to the case holding unit) extending from the chair back to the deflection unit 104 in front of the user's eyes. In FIG. 11, the case 11 is provided above the user's head, but it may be provided near the user's temporal region or below the user's head.

The control unit 105 may be provided at the lower part of the chair. The control unit 105 may be integrated into a control apparatus other than the beam-scan display apparatus 10 according to the present invention. For example, the control apparatus may be a massage control apparatus. This allows a decrease in the total number of control apparatuses.

The headphone unit 106 may be a headphone in contact with the user's ear, or a speaker provided at the back or side of the user's head.

It is to be noted that the control processing in each of the embodiments described above may be implemented by a dedicated H/W (an electric circuit, for example) or by a CPU interpreting and executing predetermined program data that allows the execution of the above described procedures stored in a memory apparatus (a ROM, a RAM, a hard disk, and so on). In this case, the program data may be installed onto the memory apparatus through a recoding medium, or may be directly executed from a recoding medium. It is to be noted that the recoding medium is, for example, a semiconductor memory such as a ROM, a RAM, and a flash memory; a magnetic disk memory such as a flexible disk and a hard disk; an optical disk such as a CD-ROM, a DVD, and a BD; and a memory card such as an SD card. In addition, the recording medium is a concept including a communication medium such as a phone line and a carrier route.

Further, it is possible to modify the embodiments of the present invention where appropriate without departing from the scope of the present invention.

INDUSTRIAL APPLICABILITY

The beam-scan display apparatus according to the present invention, in which the deflection unit is formed on the contact lens, is applicable to a display apparatus, a display system, and a display method among others.

The invention claimed is:

1. A beam-scan display apparatus that displays an image by scanning a beam on a retina of a user, said beam-scan display apparatus comprising:
    a case for housing (i) a light source which emits a beam for drawing each pixel of a plurality of pixels constituting the image, and (ii) a scan unit configured to two-dimensionally scan the beam emitted from said light source; and
    a contact lens including a deflection unit configured to deflect, toward the retina of an eye of the user wearing said case, the beam scanned by said scan unit, said contact lens being separate from said case,
    wherein said deflection unit is a hologram formed on a surface of said contact lens,
    wherein said hologram includes:
        a first interference pattern for deflecting, toward the retina of the user, a beam incident from a first direction; and
        a second interference pattern for deflecting, toward the retina of the user, a beam incident from a second direction different from the first direction,
    wherein an optical power of said first interference pattern and an optical power of said second interference pattern are equal, and
    wherein a direction in which the beam is deflected by said first interference pattern and a direction in which the beam is deflected by said second interference pattern are different.

2. The beam-scan display apparatus according to claim 1, wherein the first and second directions are directions from said scan unit toward said hologram before and after said contact lens rotates along a surface of the eye of the user by a predetermined angle.

3. The beam-scan display apparatus according to claim 1, wherein the first and second directions are directions from said scan unit toward said hologram before and after said contact lens revolves around a center of the eye of the user by a predetermined angle.

4. The beam-scan display apparatus according to claim 1, wherein said contact lens includes a rotation suppressing part which suppresses a rotation of said contact lens along a surface of the eye of the user.

5. The beam-scan display apparatus according to claim 4, wherein said rotation suppressing part is a part of said contact lens, and has a density different from a density of another part of said contact lens.

6. The beam-scan display apparatus according to claim 1, further comprising:
   a light detection unit configured to detect a reflection, from said contact lens, of the beam emitted from said light source;
   a relative position detection unit configured to detect a change in relative positions of said scan unit and said deflection unit with respect to each other, based on the reflection detected by said light detection unit; and
   a scan angle control unit configured to control a scan angle of said scan unit based on the change detected by said relative position detection unit, such that a beam incident on said deflection unit travels toward the retina of the user.

7. The beam-scan display apparatus according to claim 6, wherein said contact lens includes a characteristic point having a reflection property different from a reflection property of another part of said contact lens,
   wherein said light detection unit is configured to detect light reflected from said characteristic point, and
   wherein said relative position detection unit is configured to detect the change in the relative positions of said scan unit and said deflection unit based on a difference between a predetermined reference position of said characteristic point and a position of said characteristic point detected by said light detection unit.

8. The beam-scan display apparatus according to claim 7, wherein said characteristic point is provided closer to said scan unit than a vertex of said contact lens.

9. The beam-scan display apparatus according to claim 1, wherein said scan unit is provided more forward than said deflection unit with respect to the user.

10. The beam-scan display apparatus according to claim 1, wherein said scan unit is provided more downward than said deflection unit with respect to the user.

11. The beam-scan display apparatus according to claim 1, wherein said scan unit is provided between an ear of the user and said deflection unit in a horizontal direction of a head of the user.

12. The beam-scan display apparatus according to claim 1, wherein said case is supported only by a temporal region of the user.

13. The beam-scan display apparatus according to claim 12, wherein said case includes:
   a first part located in front of a contact position of the case, the contact position of the case being in contact with the temporal region of the user; and
   a second part located behind the contact position of the case, such that about the contact position of the case, a moment of said first part and a moment of said second part are substantially in equilibrium.

14. The beam-scan display apparatus according to claim 13,
   wherein the contact position of the case is at a base of an ear of the user, and
   wherein said second part is provided with a battery for driving said beam-scan display apparatus.

15. A vehicle mounted with the beam-scan display apparatus according to claim 1, said vehicle comprising:
   a driver seat on which a driver wearing said contact lens is seated; and
   a case holding unit configured to hold said case at a position where a beam can be scanned on said contact lens worn by the driver.

16. A method for displaying an image using a beam-scan display apparatus,
   wherein the beam-scan display apparatus includes:
   a case for housing a light source and a scan unit; and
   a contact lens which includes a deflection unit and is separate from the case,
   wherein the deflection unit is a hologram formed on a surface of the contact lens,
   wherein the hologram includes:
      a first interference pattern for deflecting, toward a retina of an eye of a user, a beam incident from a first direction; and
      a second interference pattern for deflecting, toward the retina of the eye of the user, a beam incident from a second direction different from the first direction,
   wherein an optical power of the first interference pattern and an optical power of the second interference pattern are equal,
   wherein a direction in which the beam is deflected by the first interference pattern and a direction in which the beam is deflected by the second interference pattern are different, and
   wherein said method comprises:
      emitting, from the light source, a beam for drawing each pixel of a plurality of pixels constituting the image;
      two-dimensionally scanning the beam emitted in said emitting;
      deflecting, toward the retina of the eye of the user, the beam scanned in said two-dimensionally scanning, said deflecting being performed by the deflection unit;
      detecting a reflection, from the contact lens, of the beam emitted in said emitting;
      detecting a change in relative positions of the scan unit and the deflection unit with respect to each other, based on the reflection detected in said detecting of the reflection; and
      controlling a scan angle of the scan unit based on the change detected in said detecting of the change in the relative positions, such that a beam incident on the deflection unit travels toward the retina of the user.

* * * * *